United States Patent [19]
Makino et al.

[11] Patent Number: 5,238,549
[45] Date of Patent: Aug. 24, 1993

[54] OXYGEN CONCENTRATION DETECTOR

[75] Inventors: Daisuke Makino, Ichinomiya; Masataka Naito, Kariya; Masahiro Shibata, Nagoya, all of Japan

[73] Assignees: Nippondenso Co., Ltd., Kariya; Nippon Soken, Inc., Nishio, both of Japan

[21] Appl. No.: 733,740

[22] Filed: Jul. 23, 1991

[30] Foreign Application Priority Data

Jul. 26, 1990 [JP] Japan ................... 2-198214
Jul. 3, 1991 [JP] Japan ................... 3-163111

[51] Int. Cl.$^5$ .................................. G01N 27/409
[52] U.S. Cl. .................................. 204/425; 204/424; 204/426
[58] Field of Search ................ 204/424, 425, 426

[56] References Cited

U.S. PATENT DOCUMENTS

| | | | |
|---|---|---|---|
| 4,177,112 | 12/1979 | Suzuki et al. | 204/1 T |
| 4,356,065 | 10/1982 | Dietz | 704/1 T |
| 4,402,820 | 9/1983 | Sand et al. | 204/425 |

FOREIGN PATENT DOCUMENTS

| | | |
|---|---|---|
| 0059933 | 3/1982 | European Pat. Off. . |
| 0310063 | 9/1988 | European Pat. Off. . |
| 2711880 | 3/1977 | Fed. Rep. of Germany . |
| 61-45962 | 3/1986 | Japan . |
| 2-4858 | 1/1990 | Japan . |

*Primary Examiner*—John Niebling
*Assistant Examiner*—William T. Leader
*Attorney, Agent, or Firm*—Cushman, Darby & Cushman

[57] ABSTRACT

In an oxygen concentration detector which comprises an oxygen ion-conducting solid electrolyte, a pair of electrodes, provided on both sides of the solid electrolyte, as counterposed against each other, at least one of the electrodes being exposed to a sample gas, an oxygen ion-conducting diffusion-resistant layer, provided on the electrode exposed to the sample gas and having a predetermined porosity thereby to promote the diffusion of the sample gas, the present oxygen concentration detector is characterized by an electrically insulating porous layer, made of an electrically insulating material, provided between the electrode exposed to the sample gas and the diffusion-resistant layer and having a lower porosity than that of the diffusion-resistant layer and can accurately detect an oxygen concentration of the sample gas with current-voltage characteristics free from hysteresis.

7 Claims, 12 Drawing Sheets

F I G. 1
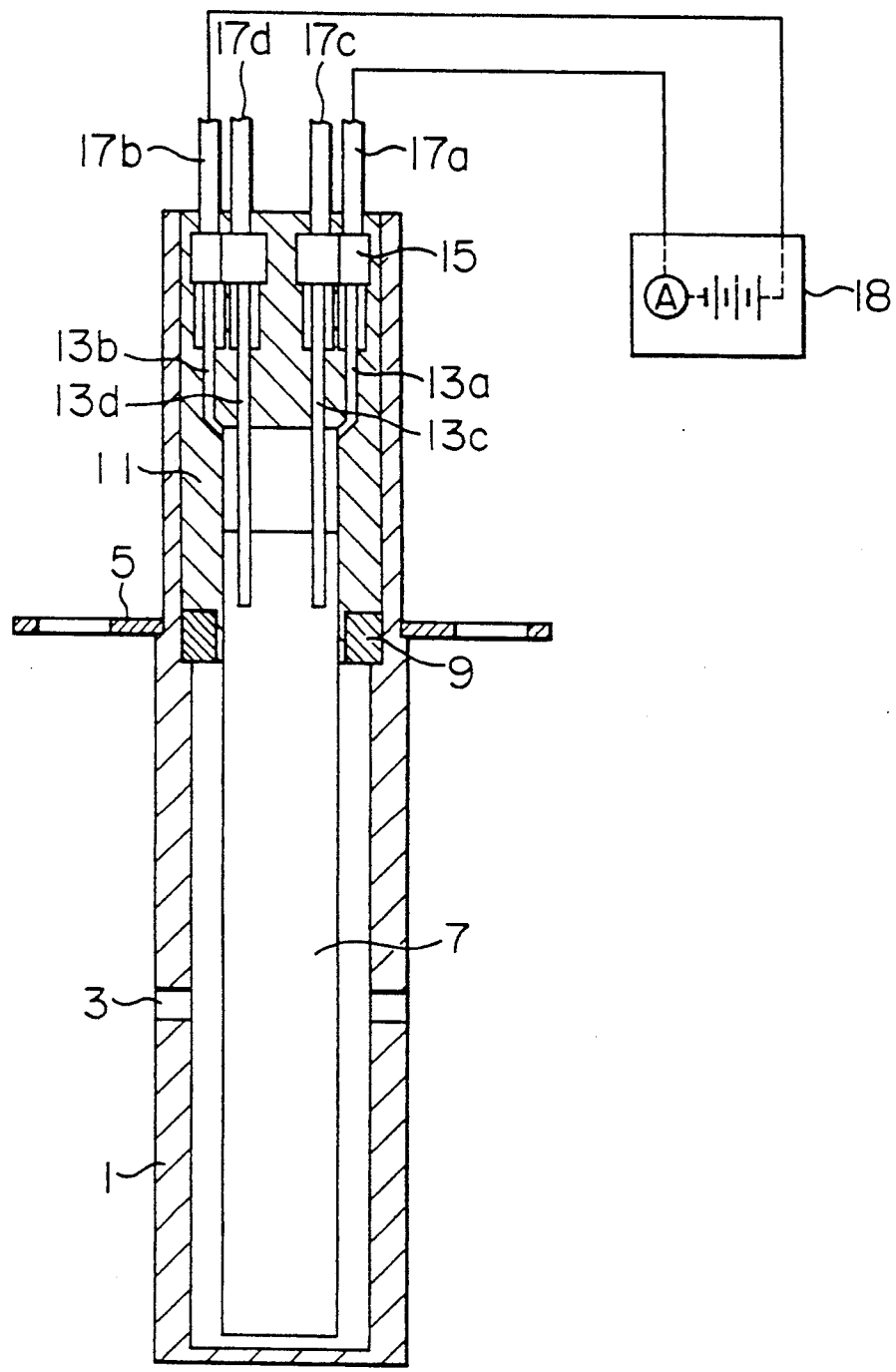

F I G. 8
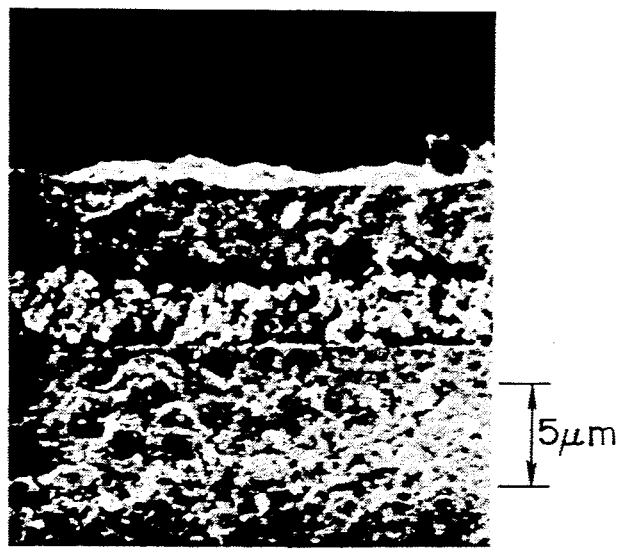
x 2000

OXYGEN CONCENTRATION DETECTOR

BACKGROUND OF THE INVENTION

1. Field of the Invention

The present invention relates to an oxygen concentration detector which detects an oxygen concentration of a sample gas from, for example, burners for hot water or internal combustion engines.

2. Prior Art

An oxygen concentration detector comprising detector electrodes coated with aluminum oxide or the like is disclosed in JP-B-2-4858 (=U.S. Pat. No. 4,356,065).

However, the detector shows no region of constant current against voltage changes, i.e. flat current region, as shown in FIG. 13. Therefore, no good limit current characteristics cannot be obtained. FIG. 13 shows the data obtained with platinum electrodes coated only with alumina as a diffusion-resistant layer.

To overcome such a disadvantage, JP-A-61-45962 proposes to provide a zirconia diffusion-resistant layer on a zirconia element in view of differences in shrinkage and thermal expansion coefficient at the firing. In this case, a constant current region (flat region) is obtained as shown in FIG. 14, but occurrence of large hysteresis in the voltage-current characteristics is a problem as obvious from FIG. 14.

SUMMARY OF THE INVENTION

The present invention has been accomplished to solve the foregoing problems.

An object of the present invention is to provide an oxygen concentration detector for accurately detecting an oxygen concentration of a gas with distinguished current-voltage characteristics free from the hysteresis.

In order to attain the above object, the present invention provides an oxygen concentration detector which comprises an oxygen ion-conducting solid electrolyte, a pair of electrodes provided on both sides of the solid electrolyte as counterposed against each other, at least one of the electrodes being exposed to a sample gas, an oxygen ion-conducting, diffusion-resistant layer provided on the electrode exposed to the sample gas and having a predetermined porosity for accelerating diffusion of the sample gas, and an electrically insulating, porous layer made of an electrically insulating material, provided between the electrode exposed to the sample gas and the diffusion-resistant layer and having a lower porosity than that of the diffusion-resistant layer.

According to the present invention, an electrically insulating, porous layer is provided between the electrode and the diffusion-resistant layer to exert an electrically insulating action, and thus no $O^{2-}$ is produced in the diffusion-resistant layer and no hysteresis is formed.

BRIEF DESCRIPTION OF THE DRAWINGS

FIG. 1 is a cross-sectional view of a sensor structure according to one embodiment of the present invention.

FIG. 8 is a micrograph showing the structure of the sintered essential parts corresponding to the parts shown in FIG. 7.

DETAILED DESCRIPTION OF THE INVENTION

Figure 2:
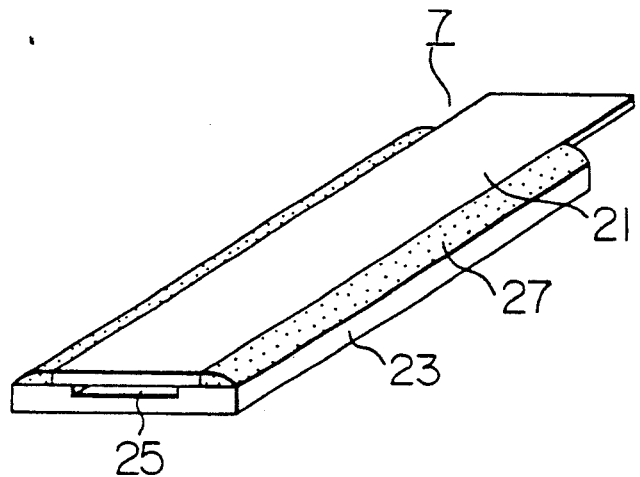
FIG. 2 is a perspective view of the sensor device according to the embodiment.

The present invention will be explained in detail below, referring to embodiments and drawings.

FIG. 1 is a cross-sectional view of the essential parts of a sensor device according to one embodiment of the present invention, where numeral 1 is a sheath made of stainless steel, 3 is a vent opening provided at the sheath 1, 5 is a flange provided at the sheath 1, 7 is a device member, 9 is an insulator for positioning and holding the device member 7 and fixed at the sheath 1 and an inorganic adhesive 11 is filled in the slight clearance between the insulator 9 and the device member 7. 13a, 13b, 13c and 13d are nickel lead wires, 15 is a terminal 17a and 17b are lead wires for voltage application and 17c and 17d are lead wires for heater. After caulking the terminals 15 and lead wires 17a, 17b, 17c and 17d, terminals 15 and nickel lead wires 13a, 13b, 13c, 13d are spot welded. Numeral 18 is a voltage application means capable of applying a voltage between the electrodes formed in the device member 7.

Figure 3:
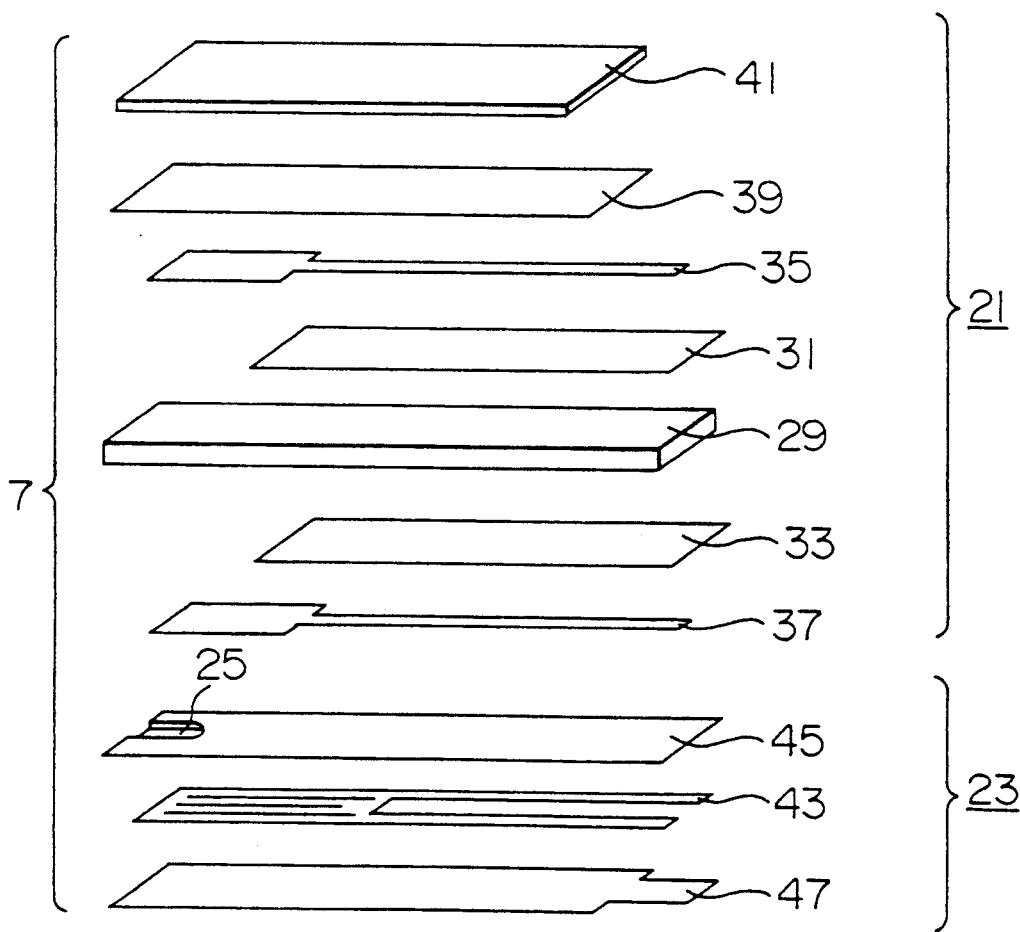
FIG. 3 is a perspective view of dismantled sensor device according to the embodiment.

FIG. 2 is a perspective view of the device member 7 according to the embodiment and FIG. 3 is a perspective view of dismantled device member 7. In FIG. 2, the device member 7 is constituted by a sensor device 21 and a heater member 23, bonded with an inorganic adhesive 27. The heater member 23 has a gas vent recess 25, and is wider than the sensor device 21. As shown in FIG. 3, the sensor device 21 has the following structure. That is, alumina insulating layers 31 and 33 for limiting the area each of electrodes are provided on both sides of zirconia element 29 as an oxygen ion conductor. Porous platinum electrodes 35 and 37 are further provided on the surfaces of the first and second alumina insulating layers 31 and 33, respectively. An alumina insulating layer 39 is provided on the surface of the platinum electrode 35 and a zirconia diffusion-resistant layer 41 is provided on the alumina insulating layer 39. On the other hand, the heater member 23 is constituted by providing alumina plates 45 and 47 on both sides of a tungsten heater 43, respectively, by lamination and the alumina plate 45 has a gas vent recess 25.

Figure 4:
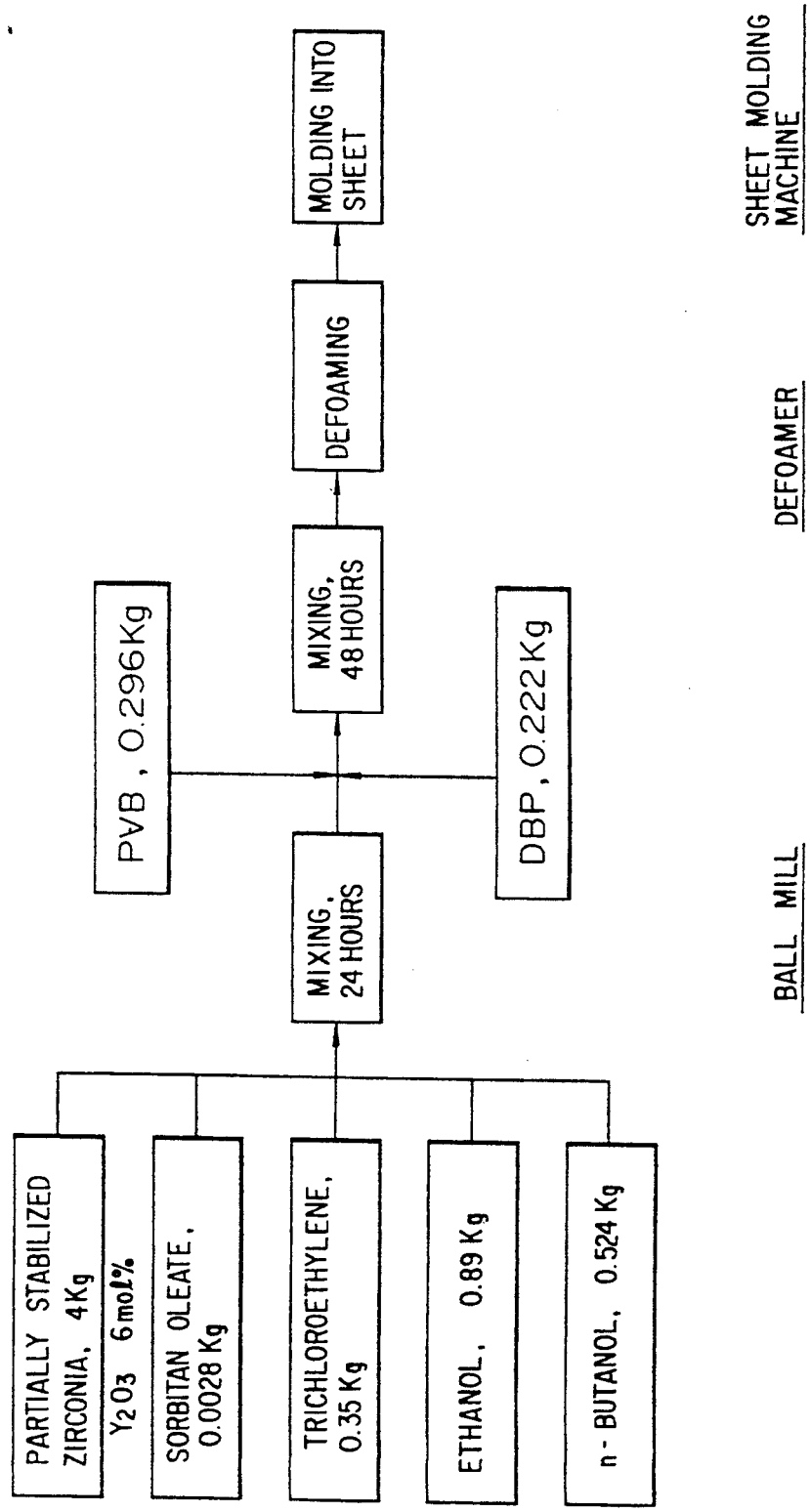
FIG. 4 is a process flow sheet showing steps of making the zirconia element according to the embodiment.

Production steps according to the embodiment of the present invention will be explained below, referring to FIGS. 4 to 6. FIG. 4 shows steps of producing a zirconia element 29. In FIG. 4 figures show amounts and time required for producing 10,000 zirconia elements 29. As shown in FIG. 4, 0.028 kg of sorbitan trioleate, 0.35 kg of trichloroethylene, 0.89 kg of ethanol and 0.524 kg of n-butanol are added to 4 kg of partially stabilized zirconia having an average particle size of 0.5 $\mu$m and containing 6% by mole of $Y_2O_3$, followed by kneading for 24 hours. Then, 0.296 kg of PVB (polyvinylbutyl alcohol) and 0.222 kg of DBP (dibutyl phthalate) are added thereto, and the mixture is kneaded for 48 hours, then defoamed and molded into a sheet to obtain a zirconia element 29. The gap between a doctor blade and the sheet is made to have a distance of 1 mm so that the molded sheet can have a thickness of 0.4 mm without any special pressure application. The zirconia element 29 is molded into a sheet in this manner by a doctor blade method.

Figure 5:
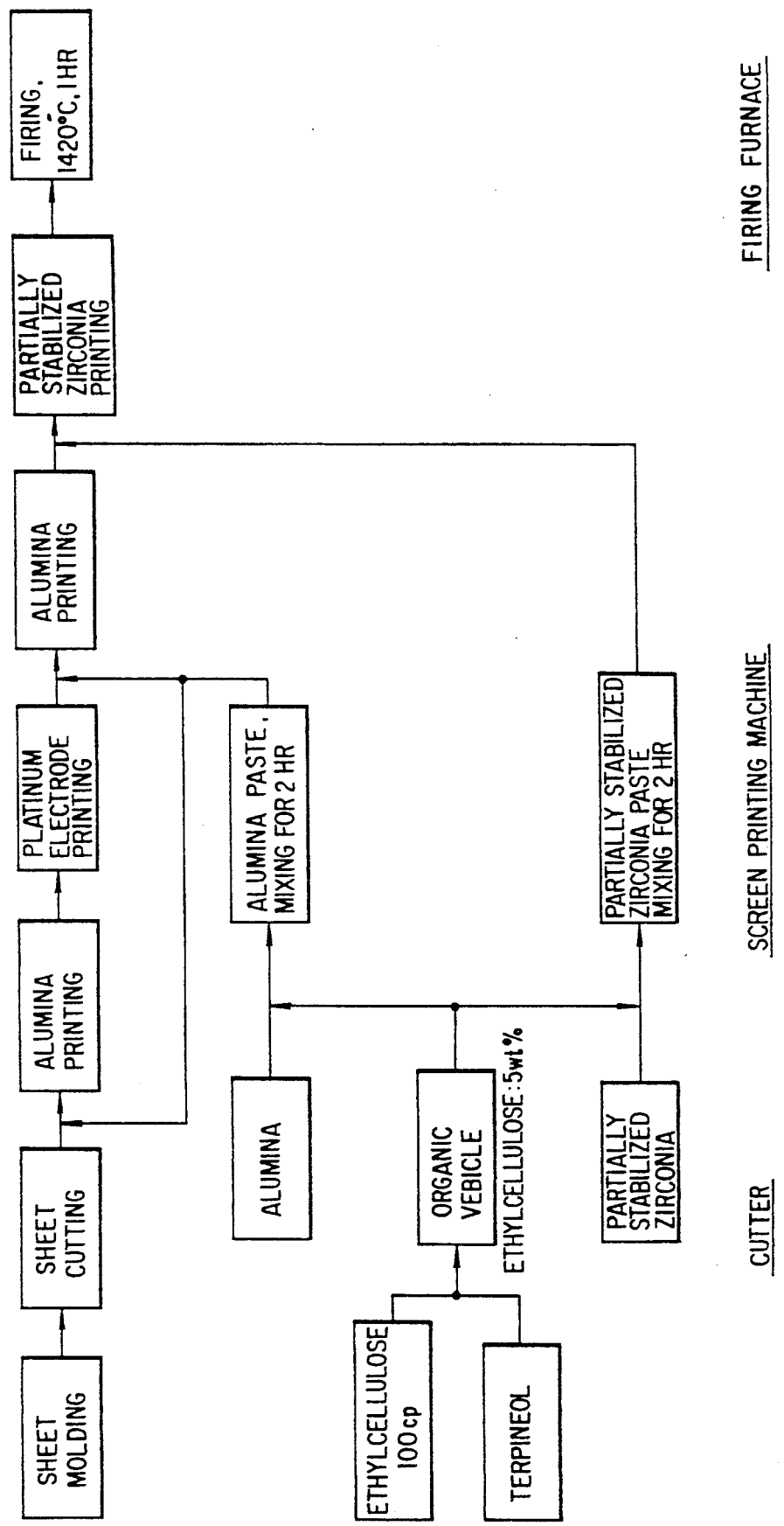
FIG. 5 is a process flow sheet showing steps of making a device according to the embodiment.

Production steps for a sensor device 21 is shown in FIG. 5. First, the molded sheet of zirconia element 29 is cut to a predetermined size (sheet cutting) and the sheet is screen printed with alumina insulating layers 31 and 33 for limiting the area each of electrodes, porous platinum electrodes 35 and 37 from a platinum paste containing 10% by weight of partially stabilized zirconia, the same material as that for the zirconia element 29, an alumina insulating layer 39 from an alumina paste, and a zirconia diffusion-resistant layer 41 from a partially stabilized zirconia paste. The resulting laminate is fired at 1420° C. In that case, the alumina paste and the partially stabilized zirconia paste are prepared as follows. Alumina having an average particle size of 0.3 $\mu$m and an organic vehicle made of 5 wt % of ethyl cellulose having a viscosity of 100 CP and 95 wt % of terpineol are mixed together in a ratio of the alumina to the organic vehicle of 20 : 32.5 by weight and then kneaded for 2 hours. Partially stabilized zirconia and the same organic vehicle as above are mixed in a ratio of the partially stabilized zirconia to the organic vehicle of 34.5 : 23 by weight and kneaded for 2 hours. Both pastes have a viscosity of 200,000 CPS. Conditions for the screen printing are as follows: 325 meshes in screen size and 25 $\mu$m in resist thickness for the alumina insulating layers 31 and 33 for limiting the area each of the electrodes; 325 meshes in screen size and 15 $\mu$m in resist thickness for the platinum electrodes 35 and 37; 325 meshes in screen size and 15 $\mu$m in resist thickness for the alumina insulating layer 39; and 325 meshes in screen size and 15 $\mu$m in resist thickness for the zirconia diffusion-resistant layer 41.

Figure 6:
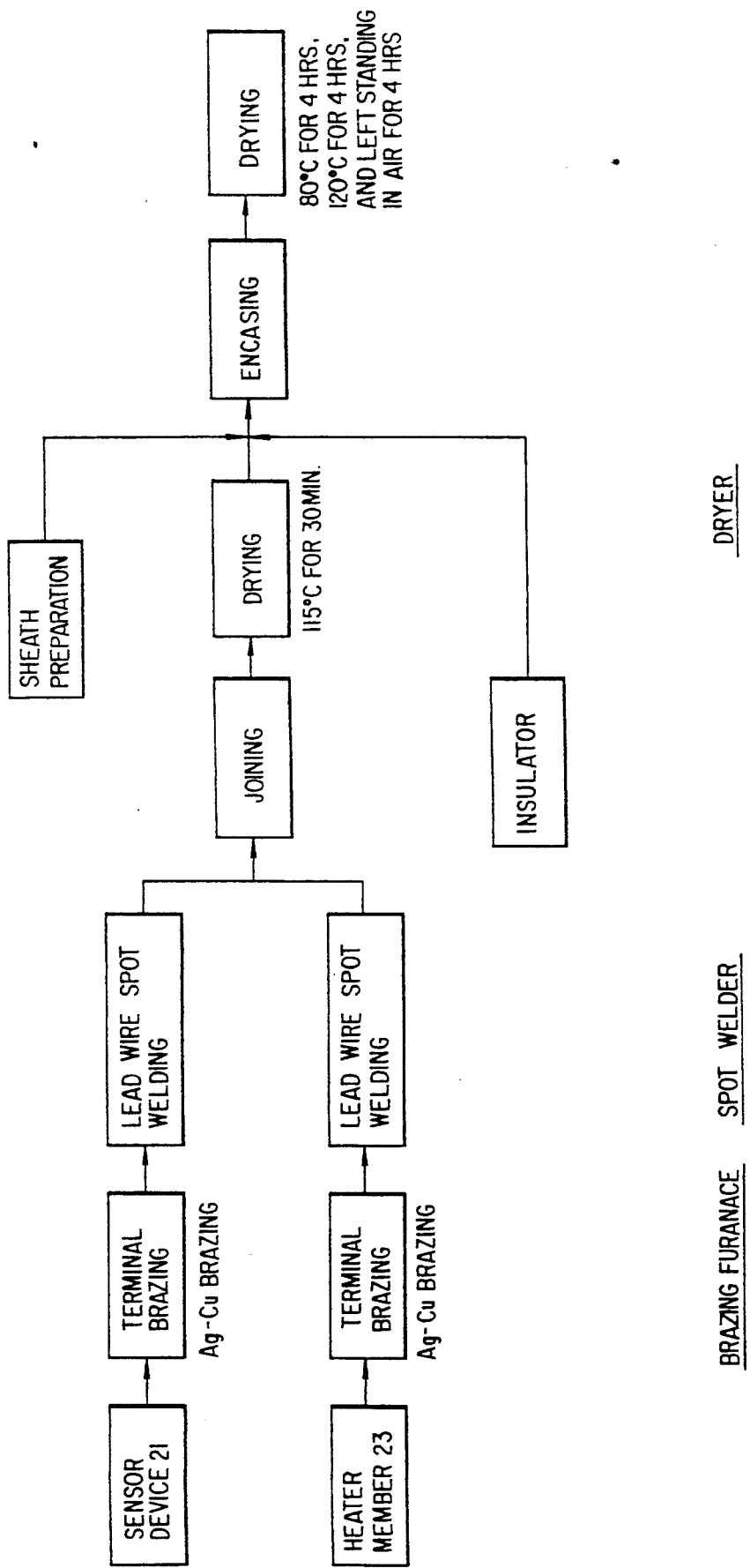
FIG. 6 is a process flow sheet showing steps of making a complete oxygen concentration detector according to the embodiment.

FIG. 6 shows steps for making a sensor device 21 and a heater member 23 into a sensor member 7 as shown in FIG. 1. Nickel lead wires 13a and 13b, and 13c and 13d are bonded to the sensor device 21 and heater member 23, respectively, by Ag-Cu brazing and lead wires 17a, 17b, 17c and 17d are connected to the nickel lead wires through terminals 15 by spot welding. The sensor device 21 and the heater member 23 are bonded to each other with an inorganic adhesive (e.g., "SUMICERAM", a trademark of a product manufactured by Sumitomo Chemical Industries, Ltd. Japan) and encased into the sheath 1.

Figure 7:
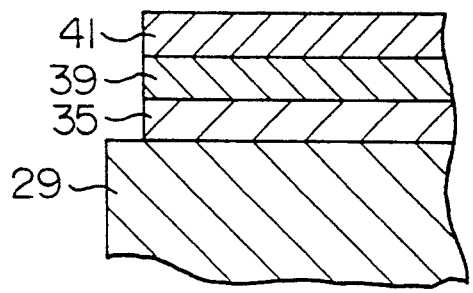
FIG. 7 is a schematic cross-sectional view showing the essential parts in the sensor device according to the embodiment.

Structure of sintered sensor device 21 in the foregoing embodiment will be explained, referring to FIG. 7 and FIG. 8. FIG. 7 is a schematic cross-sectional view of sintered essential parts of sensor device 21 and FIG. 8 is a micrograph showing the structure of the sintered essential parts. As can be seen from FIG. 8, the alumina insulating layer 39 has a lower porosity than that of zirconia diffusion-resistant layer 41, that is, the former layer is denser than the latter layer. According to the experiments conducted by the inventors, when the alumina insulating layer has a higher porosity than that of zirconia diffusion-resistant layer 41, the paste of zirconia diffusion-resistant layer 41 is brought into contact with the platinum electrode 35 and the alumina insulating layer 39 fails to fulfill the function as an insulating layer, because the printing pastes have a good flowability at the printing. As a result, a hysteresis will occur as in the prior art and thus the alumina insulating layer 39 must have a lower porosity than that of zirconia diffusion-resistant layer. The porosity of alumina insulating layer 39 can be selected as desired so long as the paste of zirconia diffusion-resistant layer will not contact the platinum electrode 35 when the zirconia paste is applied onto the alumina insulating layer by printing, without specifying a porosity range for the alumina insulating layer, because the necessary range of the porosity of alumina insulating layer depends on the viscosity of the paste for the zirconia diffusion-resistant layer 41. In this embodiment, the alumina insulating layer has a thickness of 1 $\mu$m or less, which is considerably smaller than that of zirconia diffusion-resistant layer 41, i.e. 3 to 5 $\mu$m, and that of the platinum electrode 35 i.e. 5 to 10 $\mu$m, resulting in much less influence of shrinkage at firing on the zirconia element 29 and zirconia diffusion-resistant layer 41, as will be explained later.

Working of the limit current-type oxygen concentration detector according to this embodiment will be explained below.

The limit current type oxygen concentration detector according to this embodiment is exposed to a sample gas, and then a voltage is applied between the platinum electrodes 35 and 37 by the voltage application means 18, whereby the oxygen gas in the sample gas is reduced to oxygen ions mainly at the points where the platinum electrode 35, the oxygen ion conductor and the sample gas coexist. The oxygen ions are moved through the zirconia element 29 to the interface between the zirconia element 29 and the platinum electrode 37 and oxidized to the oxygen gas again at the point where the zirconia element 29, the platinum electrode 37 and the sample gas coexist. The oxygen gas is then discharged to the outside of the device. The zirconia diffusion-resistant layer 41 provided on the platinum electrode 35 thus limits the amount per unit time of oxygen gas that can reach the coexisting point of the platinum electrode 35, the zirconia element 29 and the gas by diffusion of the sample gas, the amount per unit time of oxygen ions that is produced by reduction at the coexisting point of the platinum electrode 35, the zirconia element 29 and the gas, and the amount of per unit time of electric charge (current) that is carried by the oxygen ions, thereby passing a constant current flows irrespective of voltage within a given range.

Figure 9:
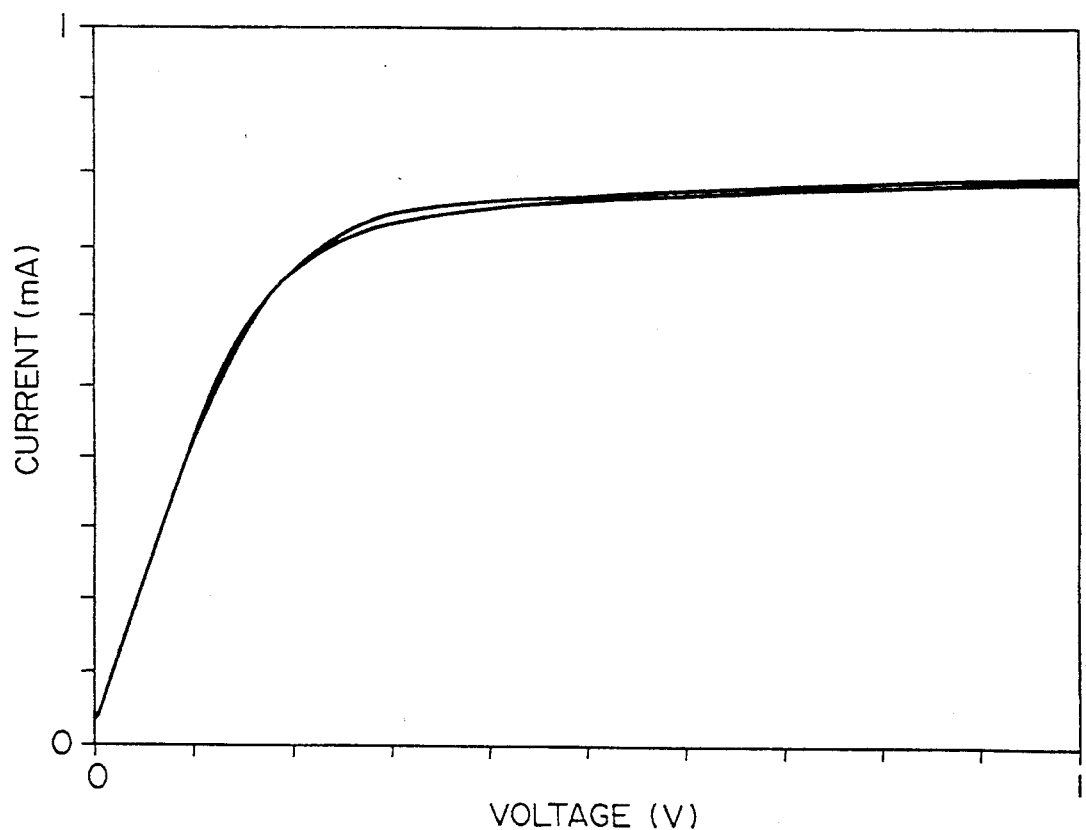
FIG. 9 is a diagram showing the current-voltage characteristics of the oxygen concentration detector made in the foregoing embodiment of the present invention.

FIG. 9 shows a current-voltage characteristic diagram of the oxygen concentration detector obtained in this embodiment. As can be seen from FIG. 9, the current necessary for the limit current type oxygen concentration detector has a constant region (flat region) without any substantial hysteresis.

Figure 10:
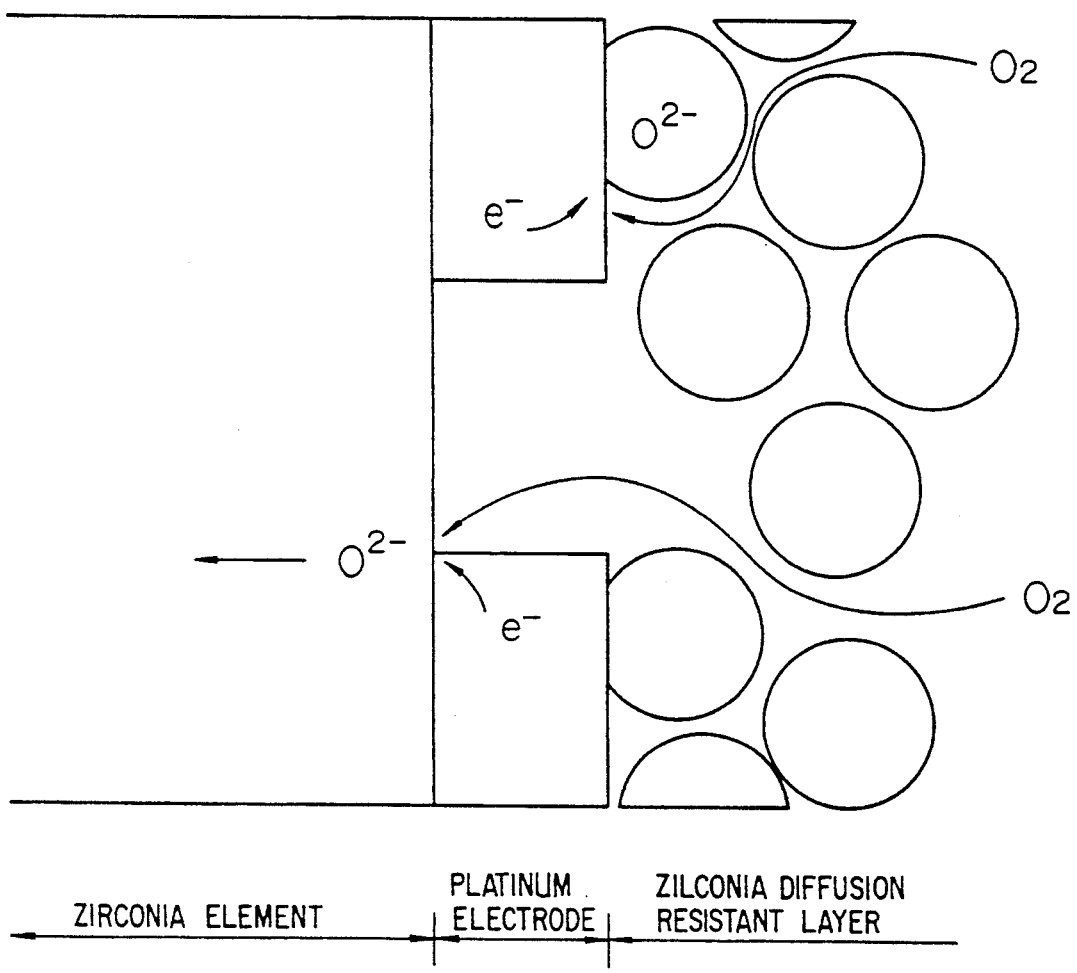
FIG. 10 is a schematic view showing the principle of function of a conventional oxygen concentration detector.
Figure 11:
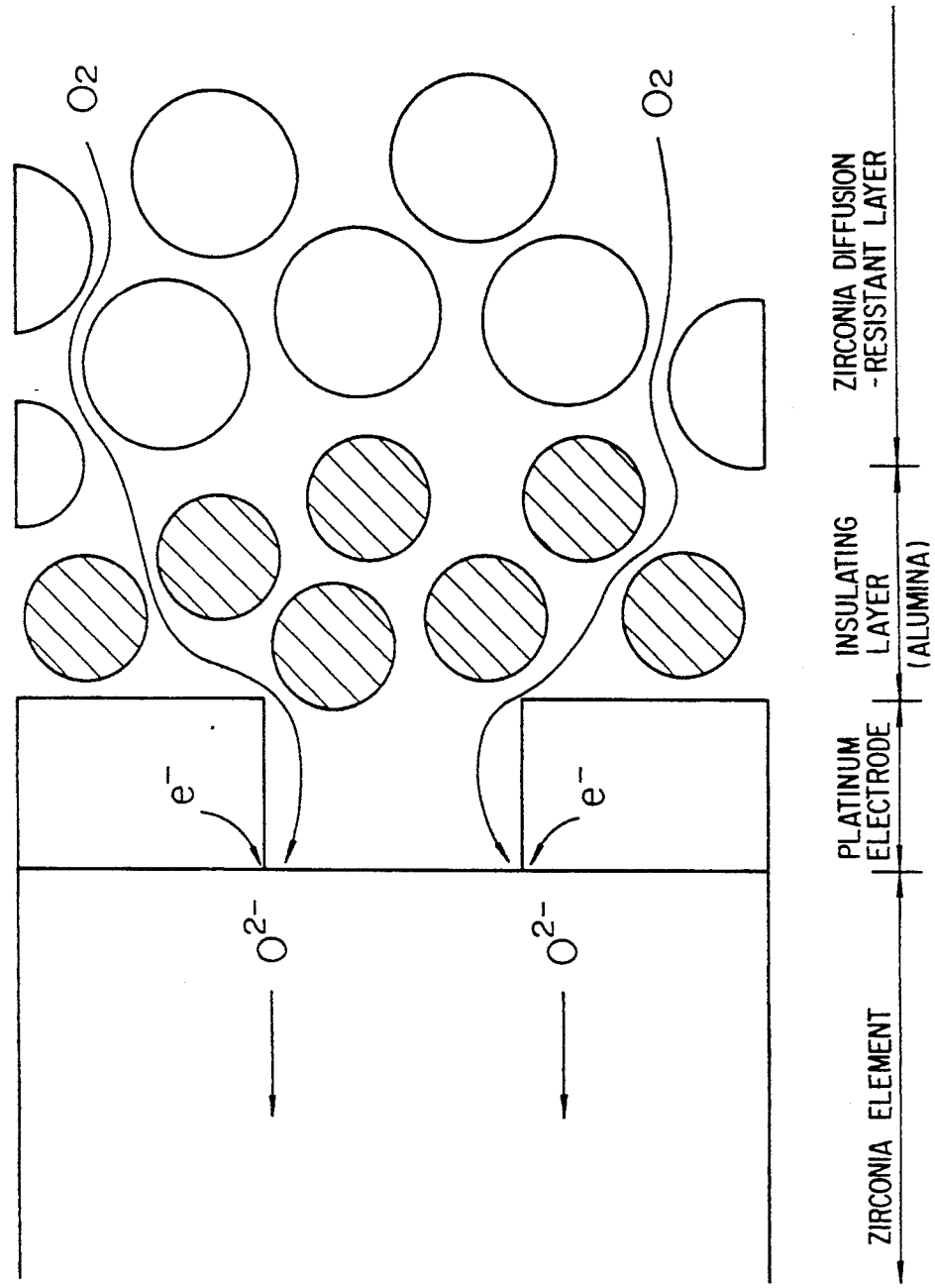
FIG. 11 is a schematic view showing the principle of function of the oxygen concentration device made in the foregoing embodiment of the present invention.
Figure 14:
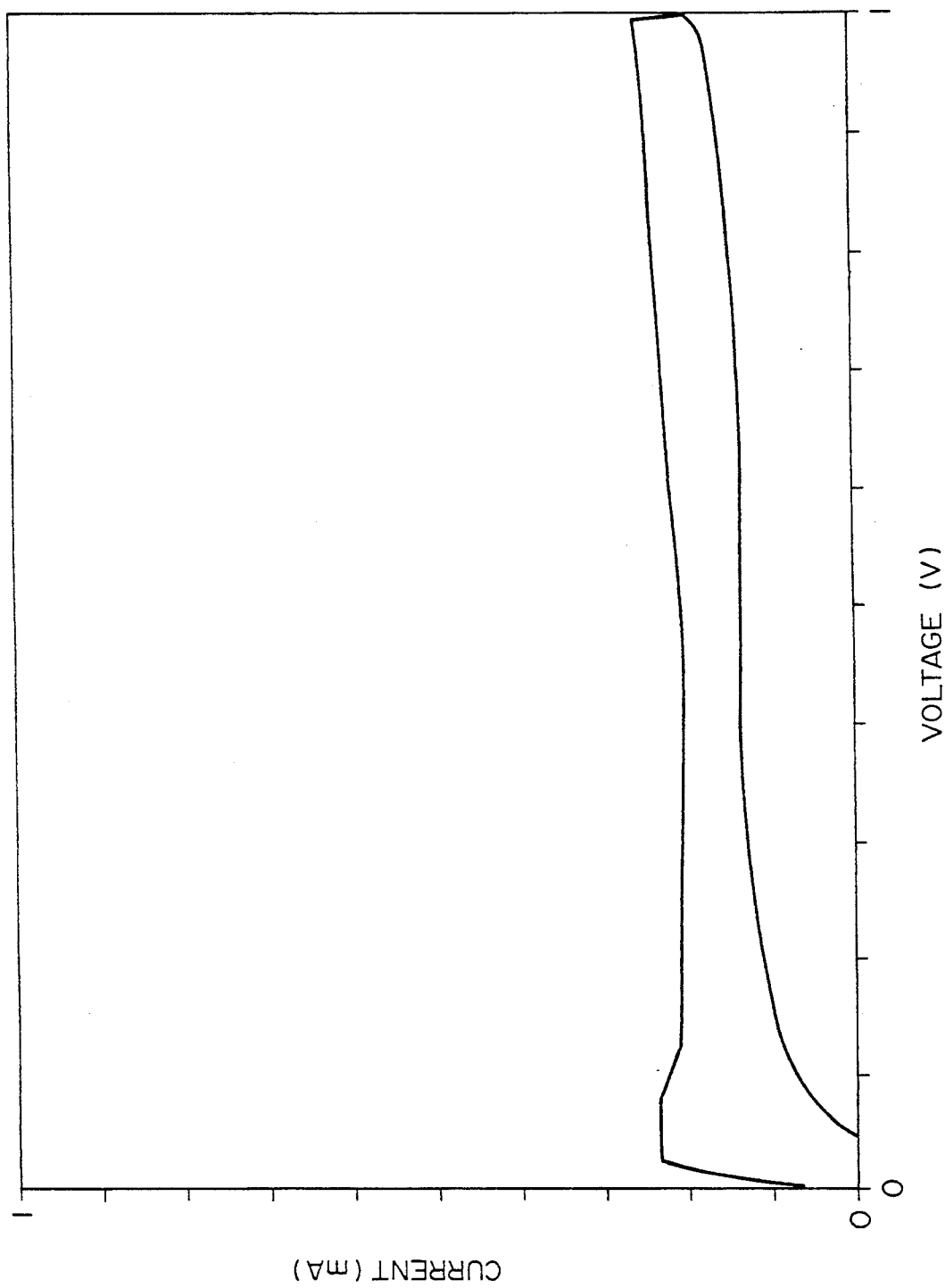
FIG. 14 is a diagram showing the current-voltage characteristics of a conventional oxygen concentration detector with a diffusion-resistant layer of zirconia.

Causes for such good results will be explained below, referring to FIGS. 10 and 11. FIG. 10 is a schematic view showing the principle of function of a conventional oxygen concentration detector and FIG. 11 is that showing the principle of function of the oxygen concentration detector according to this embodiment. Causes for hysteresis in the conventional oxygen concentration detector as shown in FIG. 14 seem to be due to the presence of a reductant and an oxidant, i.e. $O^{2-}$ and $O_2$, at the interface between the platinum electrode and the zirconia diffusion-resistant layer as shown in FIG. 10. That is, as shown in FIG. 10, in the conventional oxygen concentration detector, $O_2$ that has diffused through the zirconia diffusion resistant layer is converted to $O^{2-}$ at the interface between the platinum electrode and the zirconia element and also at the interface between the platinum electrode and the zirconia diffusion-resistant layer. Therefore, it seems that both of the $O_2$ that has diffused through pores in the zirconia diffusion-resistant layer and the $O^{2-}$ generated at the surface of the platinum electrode coexist at the interface between the platinum electrode and the zirconia diffusion-resistant layer. It is known that the current-voltage characteristics generally has a hysteresis when an oxidant (now $O_2$) and a reductant (now $O^{2-}$) coexist on the electrode (measurement by cyclic voltammetry in the electrochemistry).

The present inventors presumed that the occurrence of hysteresis can be prevented by preventing formation of $O^{2-}$ in the zirconia diffusion-resistant layer and conceived provision of an insulating layer (an alumina insulating layer in this embodiment) between the platinum electrode and the zirconia diffusion-resistant layer. Principle of function of this embodiment is shown in FIG. 11. $O^{2-}$ is not formed in the zirconia diffusion-resistant layer, because an alumina insulating layer is provided between the platinum electrode and the zirconia diffusion-resistant layer.

Figure 12:
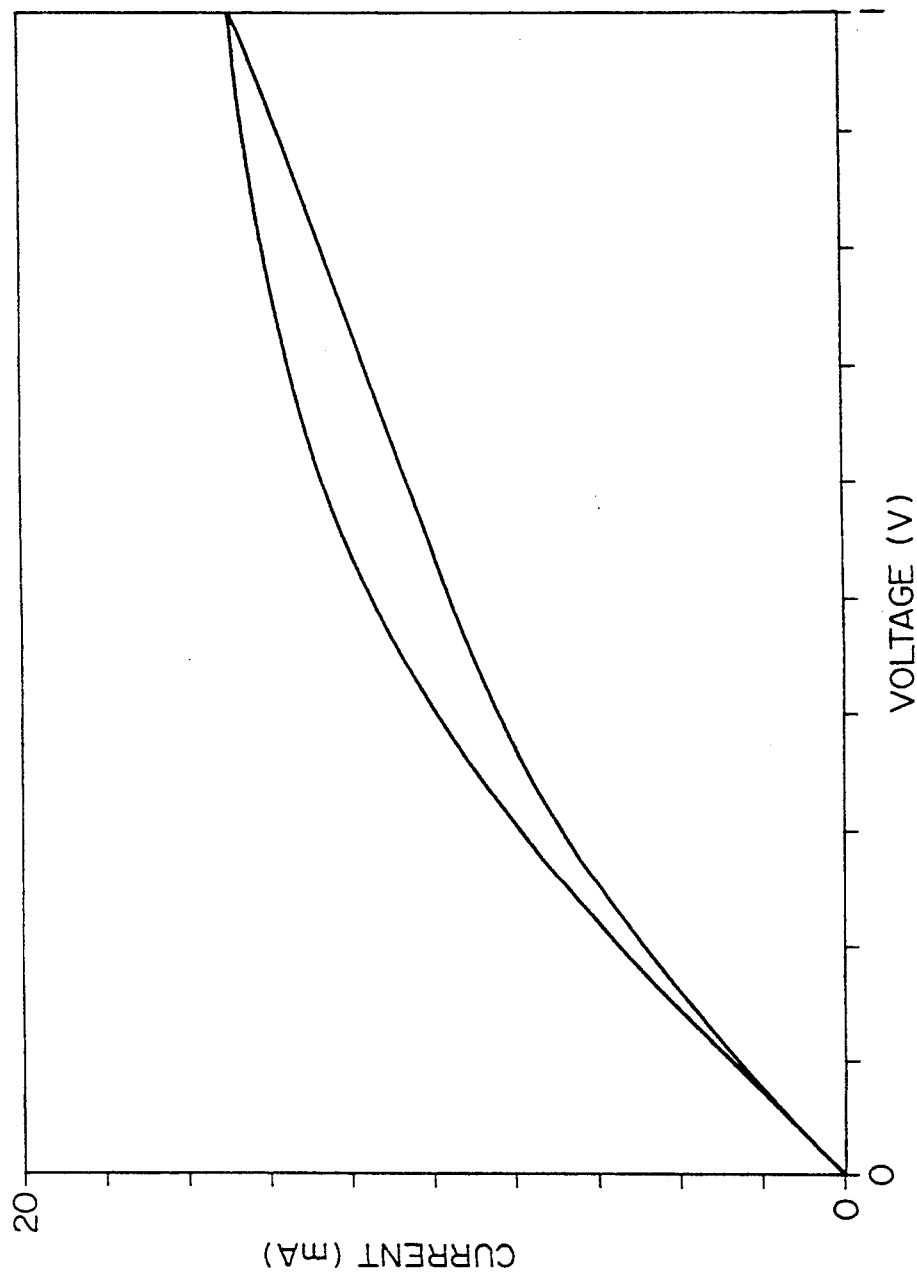
FIG. 12 is a diagram showing the current-voltage characteristics of a comparative oxygen concentration detector.
Figure 13:
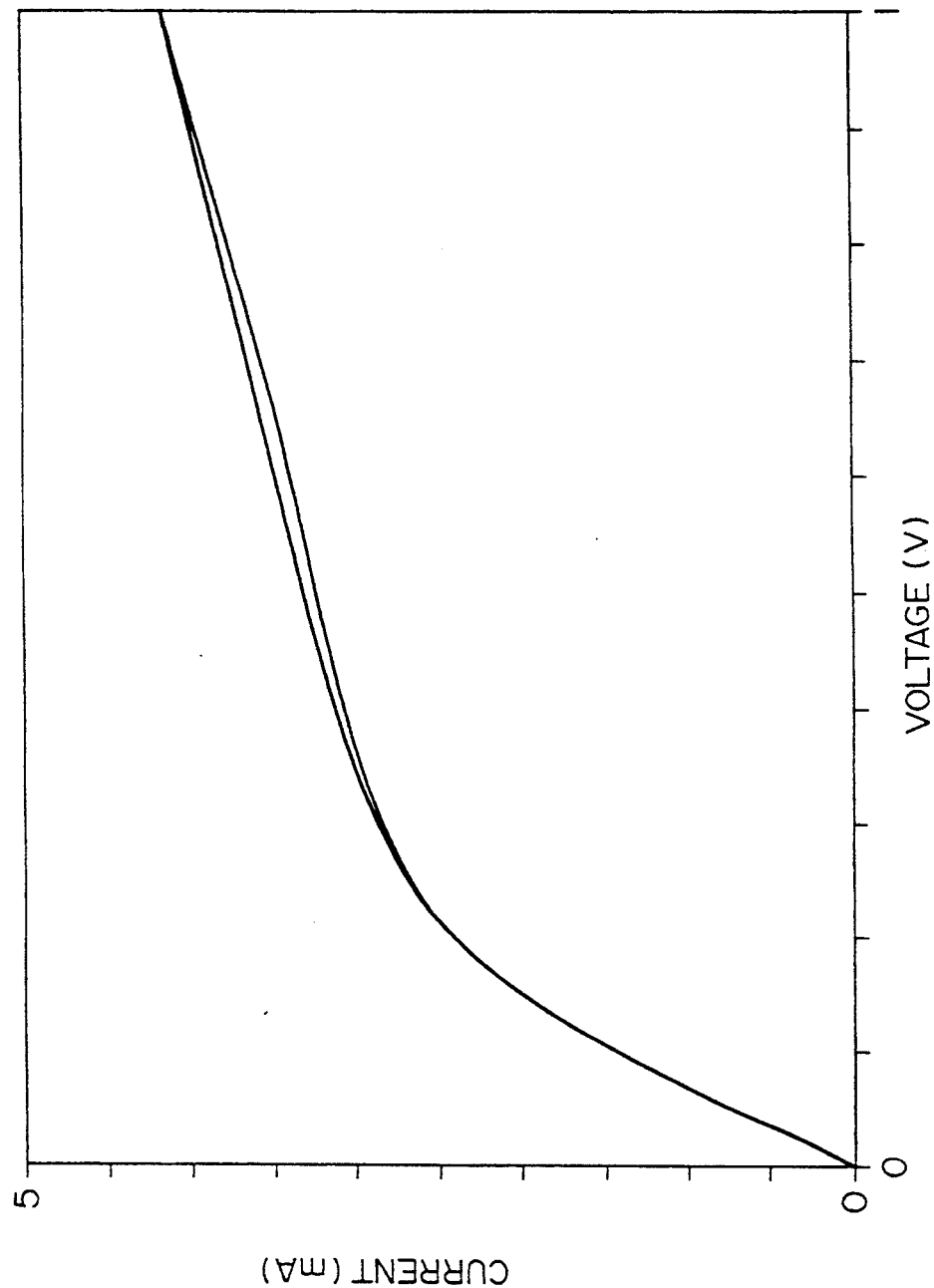
FIG. 13 is a diagram showing the current-voltage characteristics of a conventional oxygen concentration detector with a diffusion-resistant layer of alumina.

As mentioned above, too high a porosity of alumina insulating layer causes the paste of the zirconia diffusion-resistant layer to pass into the alumina insulating layer and contact the platinum electrode 35, with the result of failure in the function of alumina insulating layer 3a as an insulating layer and occurrence of hysteresis as in the conventional detector. FIG. 12 is a current-voltage characteristic diagram obtained when the porosity of alumina insulating layer 39 having an average particle size is increased to 1 μm, as experimental data for supporting this fact. Thus, hysteresis occurs as in the conventional detectors when the porosity of the alumina insulating layer is increased. However, such inconvenience can be prevented by making the porosity of alumina insulating layer 39 lower than that of zirconia diffusion-resistant layer 41 as in this embodiment. In this embodiment, the alumina insulating layer has an average particle size of about 0.3 μm.

Experiments conducted by the present inventors further reveal that when alumina insulating layer 39 has a thickness similar to that of zirconia diffusion-resistant layer, micro-cracks occur in the zirconia diffusion-resistant layer 41. Accordingly, the alumina insulating layer 39 must have a smaller thickness than that of zirconia diffusion-resistant layer 41.

In this embodiment, an alumina insulating layer is used as an electrically insulating porous layer, but in place of the alumina any other materials can be used, so far as they have a firing temperature and thermal expansion coefficient close to those of zirconia and have no ion conductivity and no ability to stabilize the zirconia. For example, $MgAl_2O_4$, $SiO_2.Al_2O_3$ can be enumerated.

Moreover, the method for formation of the layers is not limited to the screen printing method used in this embodiment, but a sputtering method or a chemical vapor deposition method (CVD method) can be also employed.

In the foregoing embodiment, the present invention is applied to a limit current-type, oxygen concentration detector, but can be applied to an oxygen concentration cell type oxygen concentration detector (n sensor) without any occurrence of hysteresis and with accurate detection of oxygen concentration.

As explained above, the present invention has the following distinguished effects. Owing to the lower porosity of the electrically insulating porous layer than that of the diffusion-resistant layer, the diffusion-resistant layer can be prevented from passing into the electrically insulating porous layer and the electrically insulating porous layer can exert a constant electrically insulating function. Therefore, $O^{2-}$ is never formed in the diffusion-resistant layer due to the presence of the electrically insulating porous layer and thus an oxygen concentration detector having hysteresis-free current-voltage characteristics can be obtained.

What is claimed is:

1. An oxygen concentration detector to detect concentration of oxygen in a sample gas comprising:
   an oxygen ion-conducting solid electrolyte shaped to provide two oppositely located sides,
   a pair of electrodes provided on both sides of the solid electrolyte to oppose each other,
   at least one of the electrodes being adapted to be exposed to the gas in which the oxygen concentration is to be detected,
   means for applying a voltage across said electrodes to cause a current to flow in dependence on an electrode reaction with oxygen in the gas reaching said one electrode;
   an oxygen ion-conducting, diffusion-resistant layer provided on the electrode exposed to the gas and having a predetermined porosity for accelerating diffusion of the gas, and
   an electrically insulating, porous layer made of an electrically insulating material, provided between the electrode exposed to the gas and the diffusion-resistant layer, said porous layer having a lower porosity than a porosity of the diffusion-resistant layer.

2. An oxygen concentration detector according to claim 1, wherein the electrically insulating porous layer is made of alumina and the diffusion-resistant layer is made of zirconia.

3. An oxygen concentration detector according to claim 1 or 2, wherein the electrically insulating porous layer has a smaller thickness than that of the diffusion-resistant layer.

4. An oxygen concentration detector to detect concentration of oxygen in a sample gas comprising:
   a solid electrolyte made of an oxygen ion-conducting material in the form of a sheet, a pair of electrodes, provided on both sides of the solid electrolyte, to oppose each other,
   means for applying a voltage across said electrodes to cause a current to flow in dependence on an electrode reaction with oxygen in the gas reaching said one electrode, an electrically insulating porous layer directly formed on one of the electrodes, and a diffusion-resistant layer made of an oxygen ion-conducting material having substantially the same thermal expansion coefficient as that of the solid electrolyte, provided directly on the electrically insulating porous layer, said diffusion resistant layer having a higher porosity than a porosity of the electrically insulating porous layer thereby to promote the diffusion of the gas.

5. An oxygen concentration detector according to claim 4, wherein the electrically insulating porous layer has substantially a same thermal expansion coefficient as that of the solid electrolyte and is made of a material failing to serve as a stabilizer for the solid electrolyte.

6. An oxygen concentration detector to detect concentration of oxygen in a sample gas comprising:
   a solid electrolyte, composed of an oxygen ion-conducting material in the form of a sheet,
   a first electrode, formed on one side of the solid electrolyte,
   a second electrode, formed on another side of the solid electrolyte in the position opposite to the first electrode,
   means for applying a voltage across said electrodes to cause a current to flow in dependence on the electrode reaction with oxygen in the gas reaching said one electrode,
   a first insulating layer formed on the first electrode thereby to control the contact area between the first electrode and the gas,
   a second insulting layer, formed on the second electrode thereby to control a contact area between the second electrode and the gas,
   a heater member, provided on the first electrode-provided side of the solid electrolyte and having a recess in a portion corresponding to the gas directly-exposed portion of the first electrode,
   an electrically insulating porous layer, provided on the second electrode-provided side of the solid electrolyte and covering at last the second insulating layer-free portion of the second electrode,
   a diffusion-resistant layer, formed on the electrically insulating porous layer, the diffusion-resistant layer being capable of diffusing the gas and made of an oxygen ion-conducting material having a higher porosity than a porosity of the electrically insulating porous layer.

7. An oxygen concentration detector according to claim 6, wherein the electrically insulating porous layer is made of a material having substantially the same thermal expansion coefficient as that of the solid electrolyte and the diffusion-resistant layer is made of the same material as of the solid electrolyte.

* * * * *